US012766098B2

(12) United States Patent
Turek et al.

(10) Patent No.: US 12,766,098 B2
(45) Date of Patent: Oct. 20, 2026

(54) SOLID CO-AMORPHOUS DISPERSION OF VALSARTAN, A METHOD FOR SYNTHETIZING THE SAME AND A MEDICAL USE OF THE DISPERSION

(71) Applicants: UNIWERSYTET HUMANISTYCZNO-PRZYRODNICZY IM JANA DLUGOSZA W CZESTOCHOWIE, Czestochowa (PL); CENTRUM BADAN MOLEKULARNYCH I MAKROMOLEKULARNYCH PAN, Lodz (PL)

(72) Inventors: Marika Turek, Mstow (PL); Ewa Rozygka-Sokolowska, Czestochowa (PL); Piotr Balczewski, Lodz (PL); Marek Koprowski, Lodz (PL); Krzysztof Owsianik, Pabianice (PL); Małgorzata Makowska-Janusik, Częstochowa (PL)

(73) Assignees: UNIWERSYTET HUMANISTYCZNO-PRZYRODNICZY IM JANA DLUGOSZA w CZESTOCHOWI, Czestochowa (PL); CENTRUM BADAN MOLEKULARNYCH I MAKROMOLEKULARNYCH PAN, Lodz (PL)

( * ) Notice: Subject to any disclaimer, the term of this patent is extended or adjusted under 35 U.S.C. 154(b) by 736 days.

(21) Appl. No.: 17/922,244

(22) PCT Filed: Apr. 29, 2021

(86) PCT No.: PCT/PL2021/000028
§ 371 (c)(1),
(2) Date: Oct. 28, 2022

(87) PCT Pub. No.: WO2021/221521
PCT Pub. Date: Nov. 4, 2021

(65) Prior Publication Data
US 2023/0172854 A1 Jun. 8, 2023

(30) Foreign Application Priority Data
Apr. 29, 2020 (PL) ........................................ 433749

(51) Int. Cl.
*A61K 9/10* (2006.01)
*A61K 31/41* (2006.01)
*A61K 31/455* (2006.01)

(52) U.S. Cl.
CPC ................ *A61K 9/10* (2013.01); *A61K 31/41* (2013.01); *A61K 31/455* (2013.01)

(58) Field of Classification Search
CPC ........ A61K 9/10; A61K 31/41; A61K 31/455; A61K 9/167; A61K 9/1694; A61K 47/10;
(Continued)

(56) References Cited

FOREIGN PATENT DOCUMENTS

CN 108794418 A 11/2018

OTHER PUBLICATIONS

International Search Report and Written Opinion of the International Searching Authority in re PCT/PL2021/000028.
(Continued)

*Primary Examiner* — Sahana S Kaup
*Assistant Examiner* — Lucy M Tien
(74) *Attorney, Agent, or Firm* — Soody Tronson; STLG Law Firm

(57) ABSTRACT

A solid co-amorphous dispersion of valsartan according to the invention is characterized in that in the amorphous solid
(Continued)

phase it contains valsartan, at least one non-toxic low molecular weight co-former capable of forming hydrogen bonds with valsartan molecules, an d at least one non-toxic amphiphilic solvent that solvates valsartan and co-former molecules, wherein the content of valsartan exceeds 40 mol % and 65 wt %, and the dispersion exhibits an increased water solubility—with respect to valsartan contained therein, in comparison with the solubility of pure valsartan. A method for synthetizing a solid co-amorphous dispersion of valsartan by mixing valsartan with a co-former, pouring a solvent over the mixture and evaporating the solvent, wherein the physical mixture of valsartan, at least one non-toxic low molecular weight co-former capable of forming hydrogen bonds with valsartan molecules, and at least one non-toxic amphiphilic solvent is formed and subjected to mixing and homogenization in a condensed-phase, at the temperature range of 20-100° C., preferably 45-100° C., whereby excess of the solvent used is stripped off at the temperature range of 20-100° C., preferably 45-100° C., to give a final product in form of a solvated solid co-amorphous dispersion of valsartan, co-former and the solvent, which dispersion exhibits an increased water solubility—with respect to valsartan contained therein, in comparison with the solubility of pure valsartan. The use of solvated solid co-amorphous dispersions of valsartan as described above, obtained as described above, in medicine and pharmacy, especially for treatment of hypertension and COVID-19 disease caused by SARS-CoV-2 virus, as a ternary formulation of valsartan, nicotinamide and a non-toxic amphiphilic solvent, preferably ethanol, n-propanol or i-propanol, characterized by increased water solubility—with respect to valsartan contained therein, in comparison with the solubility of pure valsartan, and having a dual action, resulting from the synergy of ingredients supporting the therapeutic effect of valsartan. The disclosed solid dispersion according to the invention is characterized by higher solubility in comparison with that of pure valsartan, and therefore an increased bioavailability of this drug. A number of benefits results therefrom for patients (lower amount of active substance ingested), the pharmaceutical industry (lower effective dose of the active substance in preparations, resulting in reduction of production costs) and the environment (less amount of the active substance and its metabolites not absorbed by patients and released into the environment). The appropriate selection of excipients allows for the use of the dispersion according to the invention as a drug of dual-activity, in treatment of hypertension and in treatment of SARS-CoV-2 coronavirus infection causing COVID-19 disease.

13 Claims, 4 Drawing Sheets

(58) Field of Classification Search
CPC .... A61K 47/18; A61K 9/145; A61K 2300/00; A61P 9/12
USPC .......................................................... 424/4
See application file for complete search history.

(56) References Cited

OTHER PUBLICATIONS

Valsartan for Prevention of Acute Respiratory Distress Syndrome in Hospitalized Patients With SARS-COV-2 (COVID-19) Infection Disease, Retrieved from the Internet Jun. 21, 2021 URL: https://clinicaltrials.gov/ct2/show/record/NCT04335786.

Turek Marika et al: "Role of Hydrogen Bonds in Formation of Co-amorphous Valsartan/Nicotinamide Compositions of High Solubility and Durability with Anti-hypertension and Anti-COVID-19 Potential", Molecular Pharmaceutics, vol. 18, No. 5, Apr. 1, 2021 (Apr. 1, 2021), pp. 1970-1984, XP055836308, us ISSN: 1543-8384, DOI: 10.1021/acs.molpharmaceut.0c01096 Retrieved from the Internet: UR: https://pubs.acs.org/doi/pdf/10.1021/acs.molpharmaceut.0c01096.

SOLID CO-AMORPHOUS DISPERSION OF VALSARTAN, A METHOD FOR SYNTHETIZING THE SAME AND A MEDICAL USE OF THE DISPERSION

The present invention relates to a solid co-amorphous dispersion of valsartan and its medical and pharmaceutical use. Valsartan is a drug belonging to an angiotensin II receptor antagonists group that lowers blood pressure. This drug is of special importance for patients who are intolerant to angiotensin convertase inhibitors or aldosterone receptor blockers, and its poor water-solubility results in low bioavailability. Due to its composition, as well as properties and activity, the solid co-amorphous dispersion of valsartan of the invention may be useful as an antihypertensive agent, as well as a medicament supporting treatment of infection by SARS-CoV-2 coronavirus, causing COVID-19 disease.

Amorphization is a way to improve solubility of solids. Unfortunately, amorphous solids tend to recrystallize, i.e. to spontaneously assume an ordered, energetically preferred crystalline form. Crystallization of components of amorphous mixtures usually results in loss of the solid dispersion homogeneity, this phenomenon, however, can be counteracted by introducing a stabilizer in form of a co-former [1] and thus creating a so-called co-amorphous mixture.

Co-amorphization is a promising technique allowing to improve active substances solubility, that is extremely important in medicine and in pharmacy. Co-amorphization combines the features of co-crystallization, as it utilizes a similar nature of intermolecular interactions between appropriately selected components, and amorphization, thus increasing solubility and dissolution rate of a preparation [2]. It is essential that in co-amorphous mixtures, there are heteromeric intermolecular interactions between molecules of different components of the mixture, while homomeric interactions between molecules of the same component are suppressed. Otherwise, the individual components of the mixture would crystallize.

Obtaining co-amorphous formulations allows to improve the physicochemical properties of drugs without changing their chemical structure at the level of covalent bonds [3]. Such an approach is interesting for the pharmaceutical industry, because it allows to formulate the already known active ingredients into new preparations, which active ingredients have already been tested for their biological activity and safety of use, and are covered by respective legal regulations [4]. The most frequently used route of drug administration is the oral route, however, the main disadvantage of oral forms of drugs is the poor bioavailability of active substances, usually caused by their poor solubility in water environment [5]. Therefore, various strategies are used to improve solubility of poorly soluble drugs, for example combining the active substance with another highly soluble ingredient (co-former).

Many solid pharmaceutical dispersions are known and according to the co-former used the can be divided into polymer-based mixtures and mixtures containing low molecular weight co-former (molecular weight below 900 g/mol).

Thus far (in the state of the art), polymer-based solid dispersions of valsartan have mainly been studied, using macromolecular polymers as the stabilizing agents [6-9]. The use of a polymer as a co-former causes a number of problems, such as poor miscibility of the polymer with the drug (valsartan), a tendency to phase separation, hygroscopicity of the resulting formulation and a large total weight of the final tablet with a relatively small amount of valsartan, due to the high molecular weight of the polymer constituting a so called dead mass (ballast mass) [10].

The binary co-amorphous solid dispersions of valsartan with amino acids (histidine, arginine, lysine) that exhibited up to 10-times greater solubility in water than free valsartan are known from the current state of the art [11]. However, some of the solid dispersions are unstable already after 3 months of storage, which is disadvantageous for the potential medical and pharmaceutical use of those formulations. The discussed mixtures were obtained by the solvent-free method, using a vibrating ball mill.

The recently published Chinese patent application CN108794418A has disclosed a two-component co-amorphous mixture of valsartan and nicotinamide, containing components in a molar ratio of 1:1 [12]. The mixture was prepared by dissolving valsartan in an organic solvent (methanol, ethanol, acetonitrile or acetone), adding nicotinamide and then completely removing the solvent in vacuo. The discussed mixture showed a nearly 3-fold higher valsartan solubility in water when compared to that of pure valsdrtan.

Solid dispersions of valsartan with other drugs (valsartan/cilnidipine [13], valsartan/nifedipine [14]), obtained by heating a mixture of the active substances and then cooling it quickly (so called quench cooling) are also known. The obtained solid dispersions showed an enhanced dissolution rate than their pure components, but their stability did not exceed the period of 1 month.

So far, the documents cited above [11-14] are the only literature reports on solid co-amorphous dispersions, containing valsartan and a co-former.

Solid mixtures containing irbesartan (drug from the same group as valsartan) as well as carboxylic acids and ascorbic acid as co-formers of antioxidant properties are also known [15]. The mixtures, being obtained by a mechanochemical method with an addition of ethanol, are in fact fine-crystalline eutectic mixtures and not co-amorphous ones, because they exhibit only homomeric irbesartan/irbesartan and co-former/co-former interactions, in absence of heteromeric irbesartan/co-former interactions, a possibility of forming co-amorphous mixtures is therefore excluded. Nevertheless, the mixtures showed 4-7 times greater solubility in water in comparison with pure irbesartan.

There is still unmet need to develop co-amorphous mixtures of valsartan exhibiting an increased water solubility in comparison with pure valsartan and enhanced bioavailability and also suitable for medical and pharmaceutical use.

SUMMARY OF THE INVENTION

The solid co-amorphous dispersion of valsartan according to the invention is characterized in that in an amorphous solid phase it comprises valsartan, at least one non-toxic low molecular weight co-former capable of forming hydrogen bonds with valsartan molecules, and at least one non-toxic amphiphilic solvent that solvates valsartan and co-former molecules, wherein the content of valsartan in the solvated co-amorphous solid dispersion exceeds 40 mol % and 65 wt %, and the dispersion exhibits an increased water solubility—with respect to valsartan contained therein, in comparison with the solubility of pure valsartan.

According to the invention, the valsartan content is more than 45 mol %, preferably 46-49 mol %, and more than 70 wt %, preferably 75-80 wt %. A low molecular weight co-former or a mixture of low molecular weight co-formers and an amphiphilic solvent or a mixture of amphiphilic solvents support the therapeutic effect of valsartan. The low molecular weight co-former is nicotinamide or a mixture of nicotinamide with another co-former and its content in the solid dispersion is equimolar to that of valsartan. The amphiphilic solvent is a light aliphatic alcohol, preferably ethanol, n-propanol or i-propanol, preferably anhydrous, most preferably ethanol, and its molar content in the solid dispersion is more than 2 mol %, preferably more than 5 mol %.

A method for synthesis of a solid co-amorphous dispersion of valsartan consisting in mixing valsartan with a co-former, pouring a solvent over the mixture and evaporating the solvent, is characterized in that a physical mixture of valsartan and at least one non-toxic low molecular weight co-former capable of forming hydrogen bonds with valsartan molecules, and at least one non-toxic amphiphilic solvent is formed, and the thus obtained mixture is subjected to mixing and homogenization in condensed-phase at the temperature range of 20-100° C., preferably 45-100° C., whereby excess of the solvent used is evaporated at the temperature range of 20-100° C., preferably 45-100° C., to give a final product in form of a solid solvated co-amorphous dispersion of valsartan, co-former and the solvent, which dispersion exhibits an increased water solubility—with respect to valsartan contained therein, in comparison with the solubility of pure valsartan. According to the invention, a low molecular weight co-former or a mixture of low molecular weight co-formers and an amphiphilic solvent or a mixture of amphiphilic solvents used have therapeutic activity supporting the effect of valsartan. Preferably, nicotinamide is used as low molecular weight co-former and light aliphatic alcohol, preferably ethanol, n-propanol or i-propanol, preferably anhydrous, most preferably ethanol is used as amphiphilic solvent. Optionally, an additional step of drying the final product is performed, preferably under vacuum at 45-100° C., most preferably above 55° C.

Preferably, a physical mixture of valsartan, nicotinamide and an amphiphilic solvent is formed, wherein the molar ratio of valsartan to nicotinamide is 1:1 and the volume ratio of valsartan to solvent is from 1:6.9 to 1:9.7, preferably 1:8.3, and then the obtained mixture is stirred in a closed system at the temperature range of 20-100° C., preferably 45-100° C., most preferably at the boiling point of the solvent, for 1-10 hours, preferably for 3 hours, and next thus obtained crude product is subjected to stripping off the excess solvent at the temperature range of 20-100° C., preferably 45-100° C., preferably under vacuum, in a rotary evaporator, to give a solvated co-amorphous solid dispersion of valsartan with nicotinamide, exhibiting higher water solubility in comparison with that of pure valsartan, which dispersion is then dried and stored in a desiccator.

Alternatively, a physical mixture of valsartan, nicotinamide and an amphiphilic solvent is formed, wherein the molar ratio of valsartan to nicotinamide is 1:1 and the volume ratio of valsartan to the solvent is from 1:0.83 to 1:2.48, preferably 1:1.65, and then the obtained mixture is subjected to a mechanochemical grinding at the temperature range of 20-70° C., preferably at room temperature or at the temperature of self-heating of the grinding system, for 0.5-10 hours, preferably for 1 hour, and next thus obtained crude product is optionally dissolved in the amphiphilic solvent, and then subjected to stripping off the excess solvent at the temperature range of 20-100° C., preferably 45-100° C., preferably under vacuum, in a rotary evaporator, to give a solvated solid co-amorphous dispersion of valsartan and nicotinamide, exhibiting higher water solubility in comparison with that of pure valsartan, which dispersion is then dried and stored in a desiccator.

Alternatively, a physical mixture of valsartan, nicotinamide and an amphiphilic solvent is formed, wherein the molar ratio of valsartan to nicotinamide is 1:1 and the volume ratio of valsartan to the solvent is from 1:0.83 to 1:2.48, preferably 1:1.65, and then the obtained mixture is subjected to a mechanochemical grinding in a ball or disc mill at the temperature range of 20-70° C., preferably at room temperature or at the temperature of self-heating of the grinding system, for 0.5-10 hours, preferably for 1 hour, and next thus obtained crude product is optionally dissolved in the amphiphilic solvent, and then subjected to stripping off the excess solvent at the temperature range of 20-100° C., preferably 45-100° C., preferably under vacuum, in a rotary evaporator, to give a solvated solid co-amorphous dispersion of valsartan and nicotinamide, exhibiting higher water solubility in comparison with that of pure valsartan, which dispersion is then dried and stored in a desiccator.

The invention relates also to the use of the solvated solid co-amorphous dispersions of valsartan described above, obtained by the method described above, in medicine and pharmacy, as a ternary formulation of valsartan, nicotinamide and a non-toxic amphiphilic solvent, preferably ethanol, n-propanol or i-propanol, characterized by an increased water solubility in comparison with that of pure valsartan, exhibiting a dual activity resulting from the synergy of ingredients supporting the therapeutic effect of valsartan, in particular to the use as a blood pressure lowering drug as well as an agent useful in treatment of SARS-CoV-2 coronavirus infection causing COVID-19 disease, in preventing the development of that disease, in enhancing the immune response to SARS-CoV-2, in an anti-inflammatory action in case of lung injury induced by ventilator (respirator) used to treat the symptoms of acute respiratory distress syndrome (ARDS) associated with COVID-19.

The disclosed solid dispersion is characterized by higher solubility in comparison with that of pure valsartan, and thus increased bioavailability of the drug. A number of benefits results therefrom for patients (lower amount of active substance ingested), the pharmaceutical industry (lower effective dose of the active substance in preparations, resulting in reduction of production costs) and the environment (less amount of the active substance and its metabolites not absorbed by patients and released into the environment). The appropriate selection of excipients allows for the use of the dispersion according to the invention as a drug of dual-activity, in treatment of hypertension and in treatment of SARS-CoV-2 coronavirus infection causing COVID-19 disease.

The solid co-amorphous dispersion of valsartan, the method for synthesis of the same and medical use of the dispersion according to the invention are described in detail below in working examples with reference to the accompanying figures, in which:

FIG. 1 shows a comparison of the powder diffraction patterns (PXRD, Cu) of the solid co-amorphous dispersions of valsartan (VAL) and nicotinamide (NIC) solvated with ethanol (EtOH) obtained in Examples 1-3 (VAL/NIC/EtOH-1, VAL/NIC/EtOH-2, VAL/NIC/EtOH-3), pure ingredients (VAL, NIC) and their mixtures (VAL/NIC-mix);

FIG. 2 shows the $^{1}H$ NMR spectrum ($CDCl_3$) of the solid co-amorphous dispersion of valsartan (VAL) and nicotinamide (NIC) solvated with ethanol (EtOH) obtained in Example 1 (VAL/NIC/EtOH-1), containing valsartan: 47.78 mol % (77.51 wt %), nicotinamide: 47.78 mol % (21.73 wt %), ethanol: 4.43 mol % (0.76 wt %); on the spectrum there are annotations assigning selected signals to specific functional groups of the components of the solid dispersion;

FIG. 3 shows the 1H NMR spectrum ($CDCl_3$) of the solid co-amorphous dispersion of valsartan (VAL) and nicotinamide (NIC) solvated with ethanol (EtOH) obtained in Example 2 (VAL/NIC/EtOH-2), containing valsartan: 47.14 mol % (77.32 wt %), nicotinamide: 47.14 mol % (21.68 wt %), ethanol: 5.73 mol % (0.99 wt %); on the spectrum there are annotations assigning selected signals to specific functional groups of the components of the solid dispersion;

FIG. 4 shows the 1H NMR spectrum ($CDCl_3$) of the solid co-amorphous dispersion of valsartan (VAL) and nicotinamide (NIC) solvated with ethanol (EtOH), obtained in Example 3 (VAL/NIC/EtOH-3), containing valsartan: 46.61 mol % (77.17 wt %), nicotinamide: 46.61 mol % (21.64 wt %), ethanol: 6.79 mol % (1.19 wt %); on the spectrum there are annotations assigning selected signals to specific functional groups of the components of the solid dispersion;

DETAILED DESCRIPTION OF THE INVENTION

Figure 1:
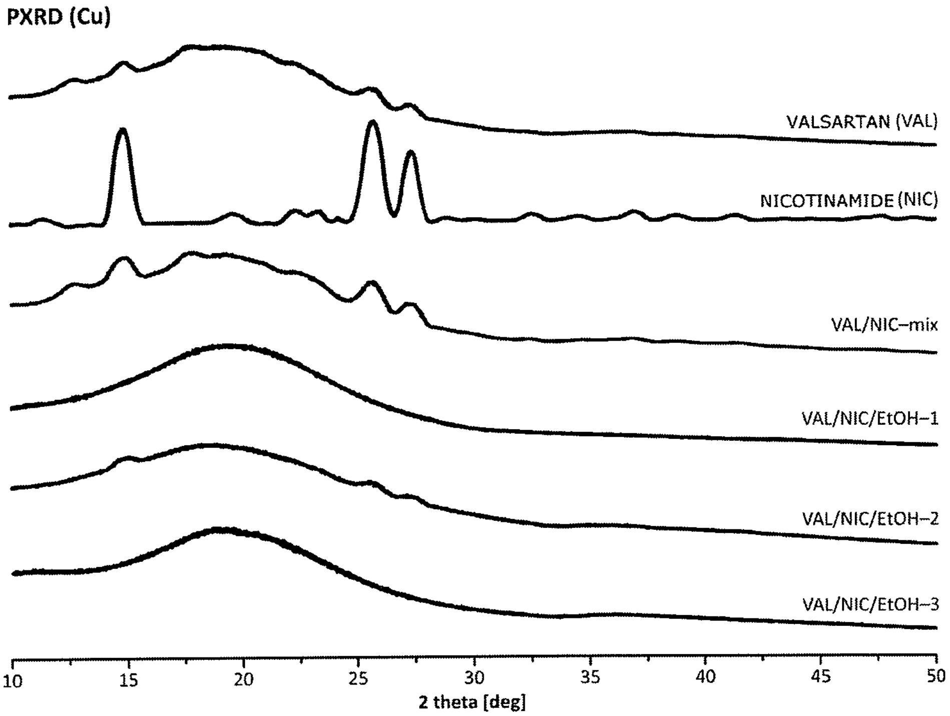
Figure 2:
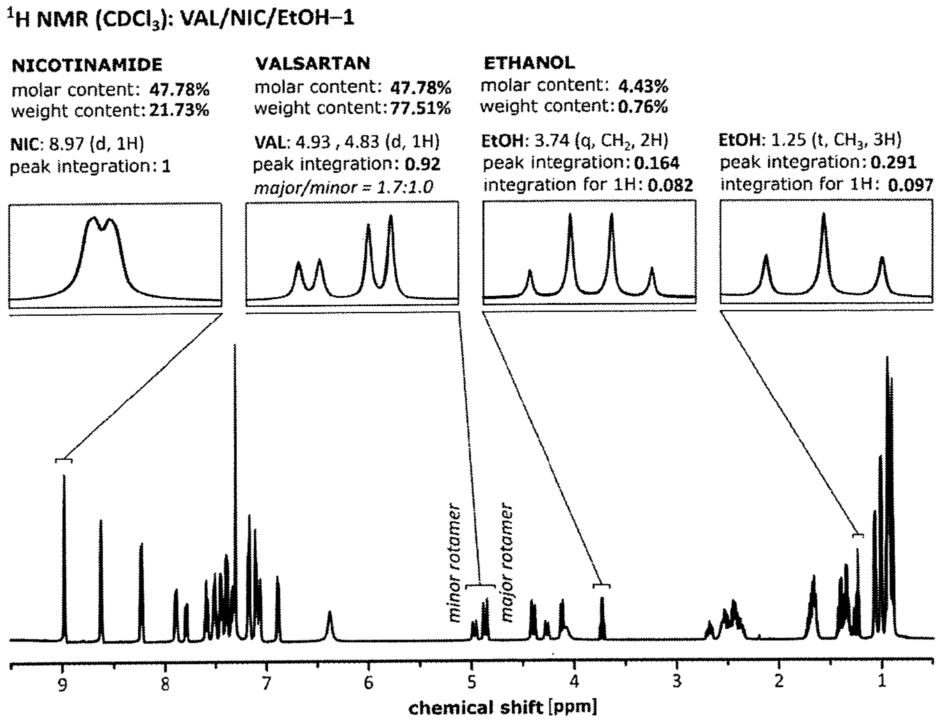
Figure 3:
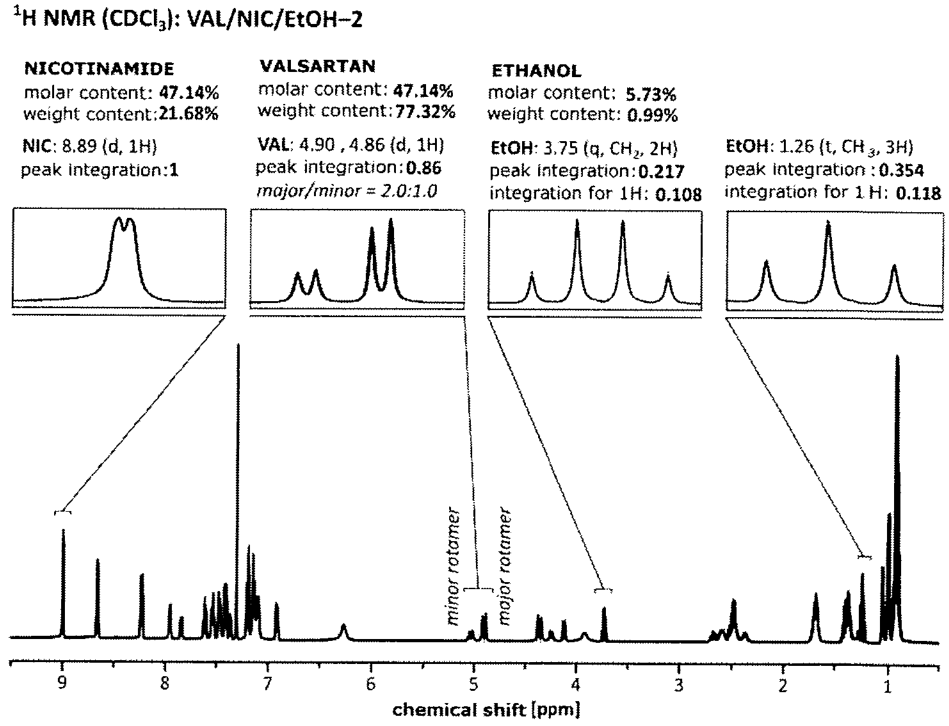
Figure 4:
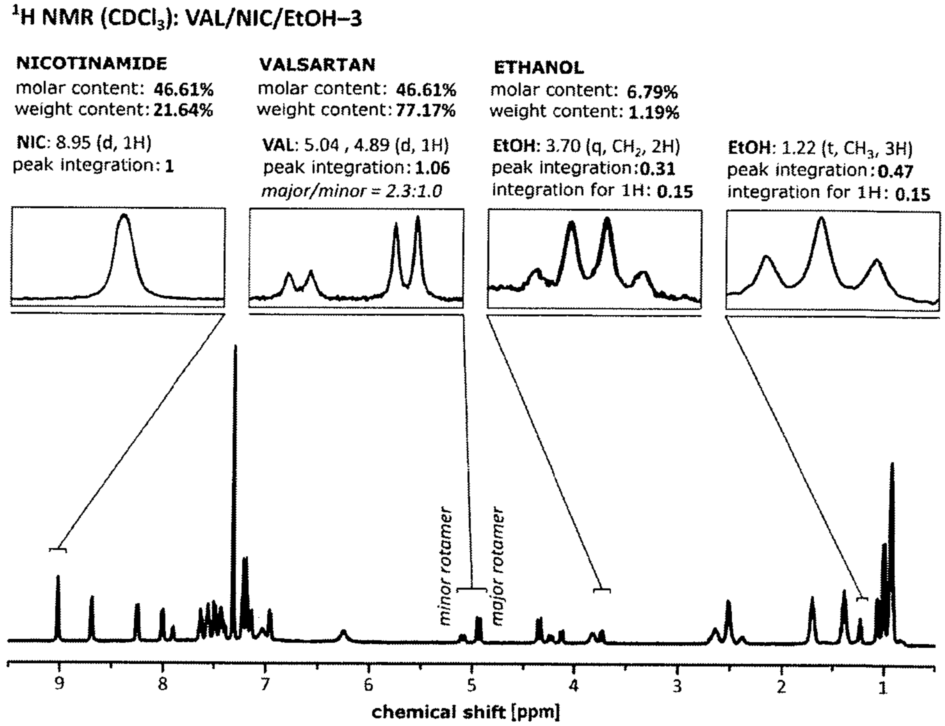

The present invention relates to a solid co-amorphous dispersion of valsartan exhibiting an increased solubility in water, and a method of its synthesis which is carried out in a condensed phase at room temperature or at an elevated temperature not exceeding 100° C., in a ternary system comprising valsartan, a co-former and an amphiphilic solvent ensuring solvation of the active pharmaceutical ingredient and the auxiliary substance, and also affects the increase of the solid dispersion solubility in water. The solid dispersion according to the invention has increased therapeutic utility due to the use of auxiliary ingredients giving supplementary medical effects. So far, the synthesis of co-amorphous mixtures, which could become a new class of drugs with dual activity resulting from the presence of both the main component of the preparation and a co-former, has not been studied in a broader scope.

Valsartan is a drug that is the main component of the preparation. Unfortunately, due to its poor solubility in water (0.16 g/L), valsartan has a low bioavailability estimated at only 25%, which results in necessity to formulate high doses of valsartan, which increases production costs and leads to material waste. In commercially available preparations, the weight content of valsartan in a tablet is usually 40-50% (for example: 47% in the single-component drug Valtap 160 mg; 45% in the two-component drug Valtap HCT 160 mg+12.5 mg). Both medicines containing 160 mg provide a bioavailability of about 40 mg of valsartan.

Recent scientific reports suggest that angiotensin II receptor antagonists (ARBs), including valsartan, may be used both in treatment of SARS-CoV-2 coronavirus infection, causing COVID-19 disease, and in prevention of the development of this disease [16, 17]. The SARS-CoV-2 coronavirus causes high mortality associated with the development of acute respiratory distress syndrome (ARDS) in infected patients. The renin-angiotensin system (RAS) plays an important role in the development of ARDS, especially the receptor of the ACE2 enzyme, to which the SARS-CoV-2 coronavirus binds and then enters the host cell. Binding (inactivation) of the ACE2 receptor by the virus results in excessive accumulation of angiotensin II which in turn stimulates angiotensin 11 type 1 receptors (AT1R). AT1R stimulation increases the permeability of the capillary-alveolar barrier, leading to an accumulation of fluid in the lungs and eventually the collapse of the alveoli. This explains the pathological changes in lungs when the activity of the ACE2 enzyme is reduced. Valsartan blocks AT1R, thereby preventing development of the pathological process described above.

The clinical trial reported on Apr. 6, 2020 (ClinicalTrials.gov ID: NCT04335786) suggested possible mechanisms of valsartan activity:

1) valsartan may block the excessive angiotensin-mediated AT1R activation;
2) valsartan may increase the activity of the ACE2 enzyme, which lowers the levels of angiotensin II and at the same time increases the production of lung-protective angiotensin (1-7)

To date, 21 clinical trials on the effects of ARBs on COVID-19 have been registered, including one on valsartan alone (ClinicalTrials.gov ID: NCT04335786). Moreover, the results of retrospective studies show that the elderly people (>65 years) suffering from COVID-19 with concomitant hypertension, taking ARBs may be more resistant to the occurrence of lung diseases related to SARS-CoV-2 than people not taking these drugs [18]. In addition, the authors of these studies suggest that ARB drugs should be subjected to clinical trials on patients infected with SARS-CoV-2 with normal blood potassium levels, normal kidney function, normal blood pressure, but also with hypertension.

According to the invention, the co-former and the solvent were chosen with regard to their general physicochemical properties as well as their suitability for human consumption and their additional medical, supportive effect and non-interfering with that of valsartan. By definition, according to the invention, a co-former is a low molecular weight compound with a molecular weight of less than 900 g/mol, having functional groups compatible with the functional groups of valsartan, i.e. those that can generate heteromeric intermolecular interactions (e.g. hydrogen bonds, dipole-dipole interactions) with aromatic, aliphatic, ketone, carbonyl and amine moieties. The solvent, on the other hand, has amphiphilic properties, i.e. it contains hydrocarbon groups that have an affinity for organic compounds to dissolve and solvate valsartan and the co-former, and also contains polar groups to increase the solubility of the entire formulation in water.

After an initial search for the optimal co-former, it was surprisingly found that valsartan forms well-soluble solid co-amorphous dispersions with nicotinamide, although the preliminary assessment of its compatibility with valsartan was moderate in light of previous reports of only a 3-fold increase in the solubility of valsartan in the co-amorphous mixture with nicotinamide [12], and about unsuccessful attempts to prepare a dispersion of co-amorphous nicotinamide with irbesartan [15]. However, this does not exclude the possibility of using a different co-former to prepare solid dispersions of valsartan, or of using a mixture of co-formers, one of which may be nicotinamide.

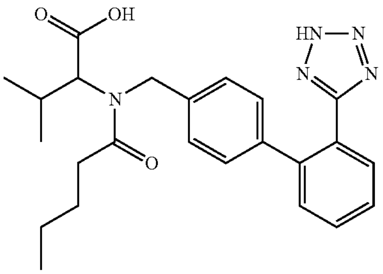

valsartan

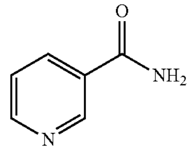

nicotinamide

After an initial search for an optimal non-toxic amphiphilic solvent for the formulation of valsartan with a co-former, alcohols, preferably light aliphatic alcohols, were selected. Solvents from this group (ethanol, n-propanol, i-propanol) have amphiphilic properties, showing very good miscibility with water and ensuring sufficient solubility of organic compounds. For objective reasons, the use of methanol, which is a strong poison and shows a relatively weak affinity for organic compounds due to its short aliphatic chain, was abandoned. On the other hand, heavier alcohols show decreased solubility in water, and butanol shows high toxicity and an unpleasant odor. Ethanol, n-propanol or i-propanol, preferably ethanol, is selected as the optimal solvent. These solvents have shown the ability to be incorporated into the structure of solid co-amorphous dispersions of valsartan with nicotinamide. However, this does not exclude the possibility of using other non-toxic amphiphilic solvents to prepare solid dispersions of valsartan, or of using a mixture of solvents, one of which may be a light aliphatic alcohol.

According to the invention, a unique pharmaceutical formulation has been developed which comprises valsartan, i.e. an antihypertensive drug. In an optimal variant, according to the invention, the solid co-amorphous dispersion of valsartan also contains nicotinamide as co-former and ethanol as amphiphilic solvent. The preparation of such a composition has a potential dualistic effect.

Valsartan is an angiotensin II receptor antagonist that reduces blood pressure and is especially important for patients who are intolerant to angiotensin converting enzyme inhibitors or aldosterone receptor blockers. There are currently 225 preparations containing valsartan in the Polish Register of Medicinal Products.

Nicotinamide has a beneficial effect on the cardiovascular system and at the same time slows down the process of degenerative arthritis [19]. In addition, nicotinamide (as well as nicotinic acid) is referred to as vitamin $B_3$, which has a beneficial effect on the human body (relaxing and reducing anxiety), which is especially important in the treatment of cardiovascular diseases. There are currently 15 nicotinamide preparations in the Polish Register of Medicinal Products. It is worth noting that nicotinamide is on the GRAS list (Generally Recognized as Safe) established by the US Food and Drug Administration (FDA), which means that it is approved for safe use as an additive for food products and can also be used as an ingredient in pharmaceutical preparations. In addition, nicotinamide can also be used in a supportive treatment of COVID-19 disease. Previous studies have shown that nicotinamide prevents lung tissue damage [20], which justifies the inclusion of supplementation with this vitamin in the diet of COVID-19 patients. With regard to SARS-CoV-2 virus infection, it is suggested that nicotinamide should be administered to infected patients with pulmonary abnormalities on CT imaging [21, 22]. It has been proven that nicotinamide is a key compound that allows to strengthen the immune response, especially in viral infections [23]. It has a strong anti-inflammatory effect in the case of ventilator-induced lung damage, which is crucial for treatment of COVID-19 [24].

Ethanol, third component of the formulation according to the invention, is a generally available foodstuff, which in pharmacy practice is used as a solvent and preservative in pharmaceutical preparations, and additionally exhibits a relaxing effect in small amounts. There are 42 preparations containing ethanol in the Polish Register of Medicinal Products.

The solid co-amorphous dispersion of valsartan according to the invention exhibits increased water solubility compared to pure valsartan, as a result of obtaining a stable co-amorphous structure provided by an appropriately selected co-former (e.g. nicotinamide), as well as the use of a small amount of amphiphilic, highly soluble excipient (e.g. ethanol, n-propanol, i-propanol). The presence of the amphiphilic solvent in the structure of the solid dispersion according to the invention allows for a significant, even 25-fold increase in the solubility of valsartan in water in comparison to that of pure valsartan. This increase in solubility was not possible using the previously reported approach assuming the formation of a co-amorphous binary mixture of valsartan with nicotinamide, without the presence of an amphiphilic solvent in the structure of the solid dispersion [12].

According to the invention, the composition of the solid dispersion and the molar ratio of the ingredients are not strictly defined, but for medical reasons, the aim should be to maximize the valsartan content. Optimal parameters of the dispersion according to the invention are obtained with an equimolar content of valsartan and co-former due to the predisposition to create a valsartan/co-former interactions in the solid phase, with valsartan/valsartan and co-former/co-former interactions being suppressed, and with a minimum solvent content. A significant excess of valsartan or a co-former in the dispersion could lead to crystallization of this component. On the other hand, excess of ethanol would not allow obtaining a solid dispersion. The increased solubility of the solid dispersion compared to pure valsartan is due to the co-amorphous structure of the formulation and the significant content of amphiphilic solvent of more than 2 mol %, preferably more than 5 mol %.

The process of producing the solid dispersion according to the invention is carried out by mixing and homogenizing the ingredients (valsartan, co-former, solvent) at the temperature in the range of 20-100° C., and then stripping off the excess solvent at the temperature range of 20-100° C., preferably 40-100° C. The elevated temperature during the homogenization step is achieved by direct heating of the reaction solution to the boiling point of the solvent or by a mechanochemical effect, in which mechanical grinding of the components heats the mixture by converting mechanical energy into heat. The elevated temperature during stripping off the excess solvent is achieved by direct heating of the system. Surprisingly, the use of the elevated temperature turned out to be crucial to obtain the highly soluble solid co-amorphous dispersion of the invention containing a substantial amount of valsartan solvating solvent and a co-former.

The positive effect of high temperature on the amorphization of solids is known, but it was expected that at the elevated temperature the solvent would be completely stripped off from the solid dispersion.

The properties and composition of the solid dispersion according to the invention depend on the synthesis method used—three exemplary variants are discussed below. However, the invention is not limited to the variants shown and also includes mixed variants as well as other procedures which include, after the physical mixture preparation: a step of high temperature mixing and homogenization of the mixture or a step of high temperature stripping off the excess solvent.

Variant 1 involves mixing of valsartan, nicotinamide and an amphiphilic solvent (ethanol, n-propanol, i-propanol) and subjecting this mixture to prolonged mixing in the liquid phase at elevated temperature. Valsartan and nicotinamide are preferably mixed in a 1:1 molar ratio, which does not preclude their mixing in other molar ratios. The volume ratio of valsartan to solvent is in the range of 1:6.9 to 1:9.7, with the best results being obtained with a volume ratio of 1:8.3. Too high solvent content results in the extension of the synthesis, while too low solvent volume results in obtaining an incompletely amorphized product. Preferably, an anhydrous solvent is used. The mixture of reagents is heated and stirred (preferably in closed system to avoid uncontrolled escape of the solvent) for 1-10 hours, preferably 3 hours, at the boiling temperature of the solvent (ethanol approx. 78° C., n-propanol approx. 82° C., i-propanol approx. 97° C.). Excess of solvent is removed from the resulting mixture, preferably under vacuum at 20-100° C., preferably at an elevated temperature above 40° C., for 30-120 minutes, preferably for 60 minutes, for example on a rotary evaporator. The resulting solid co-amorphous dispersion of valsartan and nicotinamide solvated with an amphiphilic solvent (ethanol, n-propanol, i-propanol) is stored in a desiccator where it is further dried.

Variant 2 involves mixing of valsartan, nicotinamide and an amphiphilic solvent (ethanol, n-propanol, i-propanol) and subject this mixture to a long-lasting mechanochemical treatment by using a mortar and pestle at room temperature or at an elevated temperature in the range of 20-100° C. It is possible to pre-grind the solid physical mixture of valsartan and nicotinamide and then wet it with a solvent and continue grinding, or to grind all the components together from the start of the process. Valsartan and nicotinamide are preferably mixed in a 1:1 molar ratio, which does not preclude their mixing in other molar ratios. The volume ratio of valsartan to solvent is in the range of 1:0.83 to 1:2.48, with the best results being obtained with a volume ratio of 1:1.65. Too high solvent content makes the grinding process much more difficult, lowers its efficiency and makes it impossible to obtain a solid product, while too small solvent volume results in difficulties in combining the ingredients. Preferably, small portions of the solvent are added during grinding. Preferably, an anhydrous solvent is used. The mixture of reactants is subjected to mechanical grinding in a mortar or other adapted system. The mixture heats up spontaneously as a result of grinding (local heating) or is additionally heated to a temperature of approx. 70° C. Heating-up to too high temperature leads to the boiling of the solvent, and thus makes it difficult to grind the sample. The mechanochemical treatment is carried out for 0.5-10 hours, preferably for 1 hour. Grinding in an open mortar results in a slow stripping off the solvent. Thus obtained product of grinding can be considered as final (after possible drying) or it may be dissolved in the previously used solvent, and then subjected to the process of stripping off the excess solvent at high temperature. The resulting solid co-amorphous dispersion of valsartan and nicotinamide solvated with a solvent (ethanol, n-propanol, i-propanol) is stored in a desiccator where it is further dried.

Variant 3 involves mixing of valsartan, nicotinamide and an amphiphilic solvent (ethanol, n-propanol, i-propanol) and subjecting the mixture to a high energy mechanochemical treatment in a ball (or disk) mill. It is possible to pre-grind the solid physical mixture of valsartan and nicotinamide and then wet it with a solvent and continue grinding, or to grind all the components together from the start of the process. Valsartan and nicotinamide are preferably mixed in a 1:1 molar ratio, which does not preclude their mixing in other molar ratios. The volume ratio of valsartan to solvent is in the range of 1:0.83 to 1:2.48, with the best results being obtained with a volume ratio of 1:1.65. Too high solvent content results in significant difficulties in the grinding process, a reduction in its efficiency and the inability to obtain a solid product, while too small solvent volume results in difficulties in combining the ingredients. Preferably, an anhydrous solvent is used. The mixture of reagents is subjected to mechanical grinding in a laboratory mill or other adapted system. The mixture heats up spontaneously as a result of grinding (local heating) or is additionally heated to a temperature of approx. 70° C. Heating-up to too high temperature leads to the boiling of the solvent, and thus makes it difficult to grind the sample. The mechanochemical treatment is carried out for 0.5-10 hours, preferably for 1 hour. The obtained product of milling can be considered as final (after possible drying) or it may be dissolved in the previously used solvent, and then subjected to the high-temperature process of the stripping off the excess solvent. The resulting solid co-amorphous dispersion of valsartan and nicotinamide solvated with a solvent (ethanol, n-propanol, i-propanol) is stored in a desiccator where it is further dried.

Solvated co-amorphous solid dispersions of valsartan, nicotinamide and amphiphilic solvent (ethanol, n-propanol, i-propanol) obtained according to the method of the invention are in fact three-component formulations and show similar properties regardless of the synthesis variant used. Example syntheses using anhydrous ethanol were carried out and are described in details below, in the working Examples. The obtained products were subjected to physicochemical analyzes, the results of which are shown below and in FIGS. 1-6.

X-ray diffraction analysis (PXRD, FIG. 1) proved that the obtained mixtures are homogeneous solid co-amorphous phases with diffraction patterns different from those recorded for its components (valsartan, nicotinamide) and their physical mixture. The solid dispersions obtained according to variants 1 and 3 (Examples 1 and 3) are fully amorphous and the dispersion obtained according to variant 2 (Example 2) contains traces of crystalline nicotinamide but is devoid of crystalline valsartan. The solid dispersions according to the invention do not recrystallize for at least 9 months, which proves their exceptional stability. This is extremely important in the context of the possible use of the solid dispersions according to the invention in pharmacy and medicine.

$^1$H NMR analysis in anhydrous $CDCl_3$ (FIG. 2-4) showed an equimolar proportion of valsartan (variant 1: 47.78%; variant 2: 47.14%; variant 3: 46.61%) and nicotinamide (variant 1: 47.78%; variant 2: 47.14%; variant 3: 46.61%), as well as the presence of small amounts of ethanol (variant 1: 4.43%; variant 2: 5.73%; variant 3: 6.79%) in solid dispersion.

Calorimetric analysis (DSC, FIG. 5) confirmed the amorphous nature of the tested samples. The endothermic peaks from the melting of the pure components (valsartan and nicotinamide) and their physical mixture are not visible in the thermograms of the obtained solid dispersions according to the invention. These thermograms contain only two endothermic peaks: the first at a temperature of approx. 50° C. (variant 1: 50.8° C., variant 2: 56.1° C., variant 3: 43.6° C.) corresponding to the glass transition process (similar to the state of the art [12]), the second at a temperature of approx. 90° C. (variant 1: 89.7° C., variant 2: 92.6° C., variant 3: 89.7° C.) corresponding to the desorption of ethanol. A single glass transition peak indicates the homogeneity of the samples obtained, while the lack of additional peaks resulting from melting of the samples proves their amorphous nature.

Infrared spectroscopic analysis (FTIR, FIG. 6) showed that the characteristic bands derived from the carbonyl groups of valsartan (1732 $cm^{-1}$, 1602 $cm^{-1}$) and the amide group of nicotinamide (3367 $cm^{-1}$, 3160 $cm^{-1}$, 1683 $cm^{-1}$), are broadened and shifted towards lower energies in the obtained solid co-amorphous dispersions compared to the spectra of pure components and their physical mixture. This demonstrates the participation of valsartan and nicotinamide functional groups in the formation of intermolecular bonds. Moreover, the FTIR spectra of the obtained solid dispersions are different from the spectra of the physical mixture of the components, which also confirms the presence of the valsartan-nicotinamide intermolecular interactions.

The solid co-amorphous valsartan and nicotinamide dispersion solvated with a light aliphatic alcohol (ethanol, n-propanol, i-propanol) according to the invention is significantly different from the amorphous valsartan/nicotinamide mixture described in patent application CN108794418A [12]. The solid dispersion according to the invention contains a significant amount of the permanently bound non-toxic solvent (more than 2 mol %, preferably about 5 mol %), in contrast to the earlier known solution, which does not show the presence of a solvent (methanol, ethanol, acetonitrile, acetone) in the final preparation. Due to the amorphous nature and the bound solvent (ethanol, n-propanol, i-propanol), the solid dispersion according to the invention shows up to 24-times greater solubility in water (3.87 g/L) in comparison with that of pure valsartan (0.16 g/L), while the solubility of the preparation described in CN108794418A was only 3-times higher than that of pure valsartan [12]. Moreover, the process of the synthesis according to the invention (long-lasting mixing of dispersion components, high-temperature homogenization of the sample, stripping off the solvent at high temperature) is significantly different than the process known from the state of the art [12], which involves the synthesis in the presence of 16-times more solvent at room temperature, and low temperature stripping off the solvent at 20-45° C.

The solid dispersion according to the invention is also significantly different from the eutectic mixtures of irbesartan with carboxylic acids and ascorbic acid, obtained in a mechanochemical process with the addition of ethanol [15]. The dispersions according to the invention are amorphous in contrast to eutectic mixtures which are fine crystalline in nature. Moreover, the dispersions according to the invention show heteromeric interactions in the form of hydrogen bonds between the carboxyl group of valsartan and the amide group of nicotinamide, as evidenced by FTIR spectra, where the component bands involved in the formation of hydrogen bonds are shifted towards lower energies compared to the bands in the spectra of single components. On the other hand, in eutectic mixtures known from the state of the art, only homomeric interactions of irbesartan-irbesartan and co-former-co-former have been observed [15]. It is worth noting that the synthesis process known from the state of the art envisages the use of acid co-formers, the use of which in the method according to the invention would not lead to the formation of heteromeric interactions, because then in both components carboxyl groups would dominate, which would result in the formation of acid-acid homosynthones.

Surprisingly, the use of a combination of many independent factors, such as the appropriate selection of a co-former (preferably nicotinamide) capable of formation of hydrogen bonds with valsartan molecules, the use of a slight amount of an amphiphilic solvent (a light aliphatic alcohol, preferably ethanol, n-propanol, i-propanol) and high temperature homogenization or high temperature stripping off the excess solvent leads to co-amorphous solid dispersions of valsartan with nicotinamide solvated with a solvent (ethanol, n-propanol, and i-propanol) which exhibit significantly greater water solubility in comparison with that of pure valsartan. The analysis of the exemplary synthesis products showed that the dispersion obtained according to variant 1 of the process according to the invention is more than 14-times more soluble than pure valsartan, the dispersion obtained according to variant 2 is more than 3.5-times more soluble than valsartan, and the dispersion obtained according to variant 3 is 24-times more soluble than valsartan (Table 1). Such a significant increase in solubility is due to the amorphous nature of the solid dispersions and the significant solvent content (more than 2 mol %, preferably approx. 5 mol %), which solvates valsartan and nicotinamide in the solid and enables their easier transition to the aqueous phase. In turn, the difference in solubility of the formulations obtained in different working Examples is likely to be due to insufficient optimization of the process, resulting in the dispersion containing a small amount of crystalline nicotinamide in Example 2.

The use of the solvated solid co-amorphous dispersions of valsartan according to the invention in medicine and pharmacy has the advantage that, with the greater bioavailability of the active pharmaceutical ingredients, it allows the doses of drugs administered to patients to be reduced while maintaining the same therapeutic effect. This resulted in a reduction in the burden on the patient's organism, a reduction in the consumption of valsartan and nicotinamide in the pharmaceutical industry, as well as a reduction of environmental pollution with these drugs and their metabolites.

The solid co-amorphous dispersion of valsartan according to the invention may be used as a medical agent in the treatment of hypertension and in the supplementary therapy of COVID-19 disease. The advantage of this solution is the presence of a co-former having a beneficial effect on the human body, especially on the cardiovascular system (which is important in the treatment of hypertension) and on the lungs, which are the main target of the SARS-CoV-2 virus. In addition, the solid dispersion of the invention is more bioavailable than commercially available valsartan—hence it is possible to use lower doses causing the same therapeutic effect. Furthermore, the solid dispersion according to the invention may help in preventing the development of COVID-19 disease, in enhancing the immune response to the SARS-CoV-2 virus and in having an anti-inflammatory effect for lung damage induced by ventilator used to treat the symptoms of acute respiratory distress syndrome (ARDS) accompanying COVID-19.

The solid co-amorphous dispersion of valsartan, its synthesis method and its medical use according to the invention have been described in the working Examples with reference to the tables and the drawings.

Figure 5:
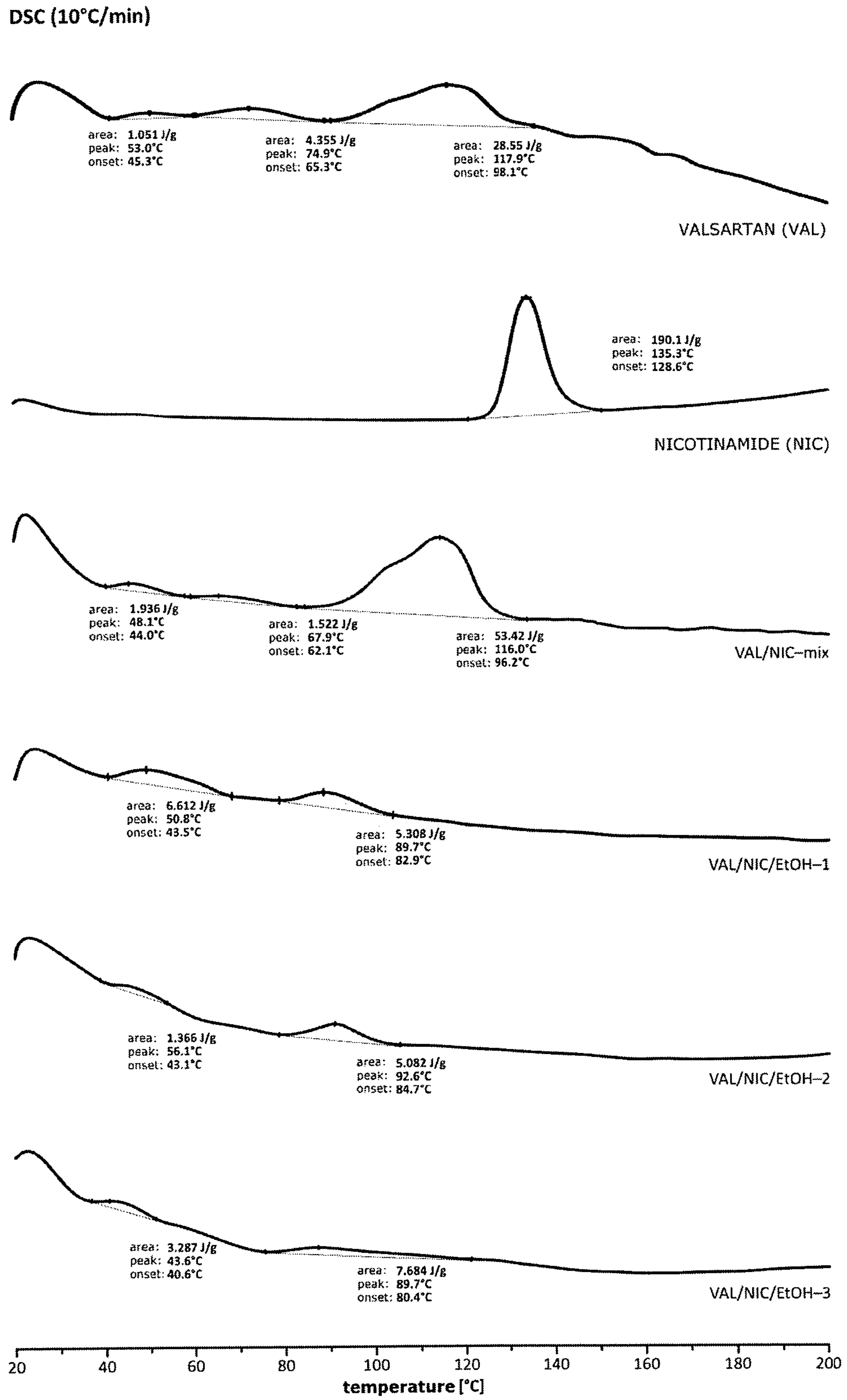
FIG. 5 shows a comparison of the calorimetric (DSC) curves of the solid co-amorphous dispersions of valsartan (VAL) and nicotinamide (NIC) solvated with ethanol (EtOH) obtained in Examples 1-3 (VAL/NIC/EtOH-1, VAL/NIC/EtOH-2, VAL/NIC/EtOH-3), as well as pure ingredients (VAL, NIC) and their physical mixture (VAL/NIC-mix); the parameters of the observed thermal signals are shown on the curves.
Figure 6:
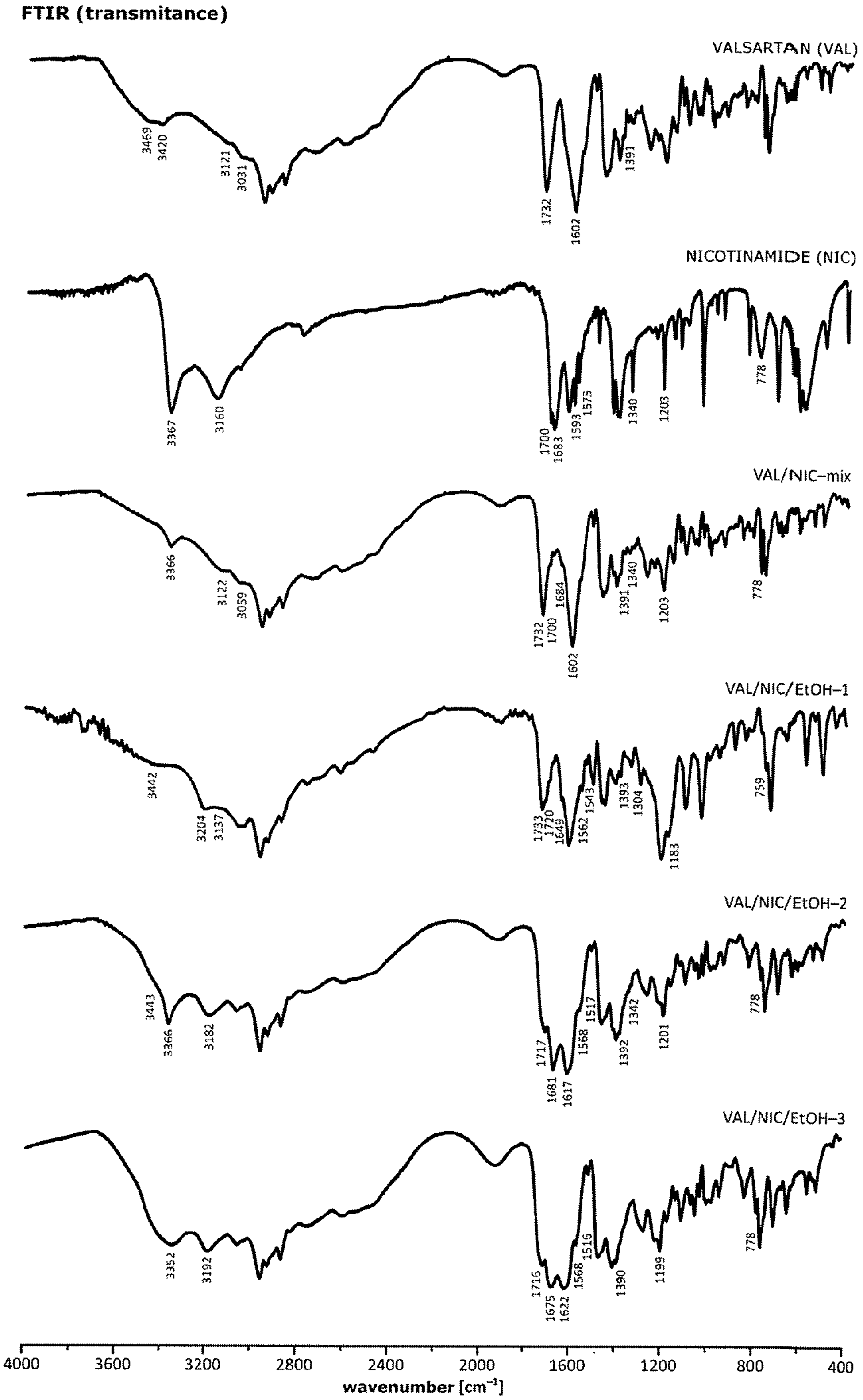
FIG. 6 shows a comparison of the infrared transmission spectra (FTIR) of the solid co-amorphous dispersions of valsartan (VAL) and nicotinamide (NIC) solvated with ethanol (EtOH) obtained in Examples 1-3 (VAL/NIC/EtOH-1, VAL/NIC/EtOH-2, VAL/NIC/EtOH-3), as well as pure ingredients (VAL, NIC) and their physical mixture (VAL/NIC-mix); the wavenumbers of the individual bands are shown on the spectra.

Example 1 (variant 1) Valsartan (435 mg, 1 mmol), nicotinamide (122 mg, 1 mmol) and anhydrous ethanol (3 mL) were mixed in a valsartan to ethanol volume ratio of 1:8.3. The resulting mixture was placed in a round bottom flask equipped with a reflux condenser and stirred for 3 hours at the reflux temperature of ethanol (78.37° C.). Then, the mixture was placed in a rotary evaporator, the solvent was evaporated and dried under vacuum (20 mbar) for 1 hour at 46° C. The obtained solid co-amorphous dispersion of valsartan and nicotinamide, solvated with ethanol, was dried and stored in a desiccator and then subjected to physicochemical analyzes. X-ray analysis (PXRD) showed that the obtained solid dispersion was a homogeneous amorphous phase as no Bragg reflections were observed in the powder diffraction pattern (FIG. 1). $^1H$ NMR analysis in anhydrous $CDCl_3$ showed an equimolar proportion of valsartan to nicotinamide and a small amount of ethanol in the solid dispersion (FIG. 2); mean integration for $^1H$ (VAL, NIC): 0.96 each; average integration for $^1H$ (EtOH): 0.089; molar composition: VAL 47.89%, NIC 47.89%, EtOH 4.21%; mass composition: VAL 77.51%, NIC 21.73%, EtOH 0.76%. The presence of ethanol in the solid dispersion was confirmed by calorimetric analysis (DSC) by recording the endothermic signal of ethanol desorption at 89.7° C. (FIG. 5). Moreover, the DSC measurements confirmed the amorphous nature of the solid dispersion, because the thermograms did not show any endothermic peaks from melting of the components and their physical mixture, and additionally, the glass transition peak of the solid dispersion was observed at 50.8° C. (FIG. 5). Infrared spectroscopic (FTIR) analysis revealed the presence of heteromeric hydrogen bonds as broadening and shifting of the valsartan carbonyl and nicotinamide amide bands towards lower energies, was observed, compared to the spectra of the pure components (FIG. 6).

Example 2 (variant 2) Valsartan (435 mg, 1 mmol) and nicotinamide (122 mg, 1 mmol) were mixed, the resulting mixture was placed in a mortar and then subjected to mechanochemical treatment. The mixture was grinded at room temperature for 60 minutes by adding an aliquot of anhydrous ethanol (0.3 mL) to the solid reagents every 30 minutes (final valsartan to ethanol volume ratio was 1:1.65), locally generating an elevated temperature due to grinding. The resulting solid co-amorphous dispersion of valsartan and nicotinamide solvated with ethanol was stored in a desiccator and then subjected to physicochemical analyzes. X-ray powder analysis (PXRD) showed that the obtained solid dispersion was a homogeneous amorphous phase as only weak Bragg reflections from the unreacted nicotinamide fraction were observed in the powder diffraction pattern (FIG. 1). $^1H$ NMR analysis in anhydrous $CDCl_3$ showed an equimolar proportion of valsartan to nicotinamide and a small amount of ethanol in the solid dispersion (FIG. 3); mean integration for $^1H$ (VAL, NIC): 0.93 each; average integration for $^1H$ (EtOH): 0.113; molar composition: VAL47.14%, NIC47.14%, EtOH 5.73%; mass composition: VAL 77.32%, NIC 21.68%, EtOH 0.99%. The presence of ethanol in the solid dispersion was confirmed by calorimetric analysis (DSC) by recording the endothermic signal of ethanol desorption at 92.6° C. (FIG. 5). The amorphous nature of the solid dispersion was confirmed because the thermograms did not show any endothermic peaks from the melting of the components and their physical mixture, and additionally, the glass transition peak of the solid dispersion was observed at 43.1° C. (FIG. 5). Infrared spectroscopic (FTIR) analysis revealed the presence of heteromeric hydrogen bonds as broadening and shifting of the valsartan carbonyl and nicotinamide amide bands towards lower energies, was observed, compared to the spectra of the pure components (FIG. 6).

Example 3 (variant 3) Valsartan (435 mg, 1 mmol) and nicotinamide (122 mg, 1 mmol) and anhydrous ethanol (0.6 mL) were mixed (valsartan to ethanol volume ratio was 1:1.65). The components were milled in an orbital ball mill for 60 minutes at 450 rpm. During grinding, the temperature of the system increased to approx. 30-35° C., and even more than 45° C. The obtained product of grinding (as paste, difficult to extract from a ball mill) was dissolved in anhydrous ethanol, then the solvent was evaporated on a rotary evaporator and dried under vacuum (20 mbar) for 1 hour at 50° C., followed by further drying for 30 minutes using an oil pump (0.7 mbar) at a temperature of 60° C. The obtained co-amorphous solid dispersion of valsartan and nicotinamide solvated with ethanol was stored in a desiccator and then subjected to physicochemical analyzes. X-ray analysis (PXRD) showed that the obtained solid dispersion was a homogeneous amorphous phase as no Bragg reflections were observed in the powder diffraction pattern (FIG. 1). $^1H$ NMR analysis in anhydrous $CDCl_3$ showed an equimolar proportion of valsartan to nicotinamide and the presence of a small amount of ethanol in the solid dispersion (FIG. 4); mean integration for $^1H$ (VAL, NIC): 1.03 each; average integration for 1H (EtOH): 0.15; molar composition: VAL 46.61%, NIC 46.61%, EtOH 6.79%; mass composition: VAL 77.17%, NIC 21.64%, EtOH 1.19%. The presence of ethanol in the solid dispersion was confirmed by calorimetric analysis (DSC) by recording the endothermic ethanol desorption signal at 89.7° C. (FIG. 5). The amorphous nature of the solid dispersion was confirmed, because the thermograms did not show any endothermic peaks from the melting of the components and their physical mixture, and additionally, the glass transition peak of the solid dispersion was observed at 43.6° C. (FIG. 5). Infrared spectroscopic (FTIR) analysis revealed the presence of heteromeric hydrogen bonds as broadening and shifting of the valsartan carbonyl and nicotinamide amide bands towards lower energies, was observed, compared to the spectra of the pure components (FIG. 6).

Example 4 (dissolution studies) Solvated solid co-amorphous dispersions of valsartan, nicotinamide and ethanol prepared as in Examples 1, 2 and 3 were subjected to water solubility tests at 37° C. The results were compared with the solubility of pure valsartan and are shown in Table 1, with absolute solubility results in parentheses and the solubility values recalculated in reference to pure valsartan. The obtained solvated co-amorphous solid dispersions were characterized by increased solubility in comparison with that of pure valsartan: the dispersion obtained in the Example 1 of the process of the invention showed a 14-fold increase in solubility, the dispersion obtained in the Example 2 showed a 3.5-fold increase in solubility, and the dispersion obtained in the Example 3 showed a 24-fold increase in solubility.

TABLE 1

Solubility of free valsartan and the obtained solid dispersions in water (the solubility of the solid dispersions recalculated in reference to pure valsartan is given in parentheses). Number of repetitions, n = 3.

| Solid form | Water solubility at 37° C. [g/L] |
|---|---|
| valsartan | 0.16 ± 0.05 |
| solid dispersion obtained in Example 1 | 2.93 (2.27) ± 0.06 |
| solid dispersion obtained in Example 2 | 0.74 (0.57) ± 0.16 |
| solid dispersion obtained in Example 3 | 5.01 (3.87) ± 0.76 |

Example 5 (stability tests) Solvated solid co-amorphous dispersions of valsartan, nicotinamide and ethanol prepared as in Examples 1, 2 and 3 were subjected to stability tests over the period of time. The tested dispersions showed durability and stability for the period of 9 months, i.e. during this time the dispersions remained amorphous and their physicochemical parameters remained unchanged compared to the freshly obtained samples.

Example 6 (medical/pharmaceutical use) A tablet of a total weight of 261.4 mg containing solvated co-amorphous valsartan dispersion prepared in Example 1 (140 mg valsartan, 40 mg nicotinamide and 1.4 mg ethanol) and classic excipients (cellulose microcrystalline, colloidal silica, magnesium carbonate, crospovidone) in which the total valsartan content by weight was 53.5%, was prepared. The prepared tablet contained lower absolute content of valsartan compared to the commercial drug containing pure valsartan (Valtap 160 mg) (Table 2), however was characterized by an increased effective amount of valsartan entering the aqueous phase during dissolution.

TABLE 2

Comparison of the composition of a tablet prepared in Example 6 containing a solid dispersion of valsartan, nicotinamide and ethanol obtained in Example 1, and a commercial available tablet of VALTAP containing 160 mg of valsartan.

| Ingredient | Composition of tablets from Example 6 | | Composition of tablet VALTAP | |
|---|---|---|---|---|
| valsartan | 140 mg | 53.5% | 160 mg | 47% |
| nicotinamide | 40 mg | 15% | — | — |
| ethanol | 1.4 mg | 0.5% | — | — |
| excipients | 80 mg | 31% | 182 mg | 53% |

Example 7 (use of i-propanol) Solvated co-amorphous solid dispersions of valsartan and nicotinamide were prepared as in Examples 1-6 with the only difference being that i-propanol was used instead of ethanol and heating, according to variant 1, was carried out at the boiling point of i-propanol. The solid co-amorphous dispersions of valsartan, nicotinamide and i-propanol with properties similar to those obtained with the use of ethanol were obtained.

CITED LITERATURE

[01] K. Löbmann, K. T. Jensen, R. Laitinen, T. Rades, C. Strachan, H. Grohganz, *Stabilized amorphous solid dispersions with small molecule excipients*. Amorphous Solid Dispersions (Eds.; N. Shah, H. Sandhu, D. S. Choi, H. Chokshi, A. W. Malick), Springer: New York, USA (2014) 613-636.

[02] R. B. Chavan, R. Thipparaboina, D. Kumar, N. R. Shastri, *Int. J. Pharm.,* 515 (2016) 403-415.

[03] D. J. Berry, J. W. Steed, *Adv. Drug Deliv. Rev.,* 117 (2017) 3-24.

[04] L. Padrela, M. A. Rodrigues, A. Duarte, A. M. A. Dias, M. E. M. Braga, H. C. de Sousa, *Adv. Drug. Deliv. Rev.,* 131 (2018) 22-78.

[05] K. H. Edward, D. Li, *Chapter 7: Solubility* [in:] Drug Like Properties: Concept, Structure, Design and Methods, from ADME to Toxicity Optimization, Elsevier (2008).

[06] W. J. Xu, H. J. Xie, Q. R. Cao, L. L. Shi, Y. Cao, X. Y. Zhu, J. H. Ciu, *Drug Deliver.,* 23 (2016) 41-48.

[07] Y. D. Yan, J. H. Sung, K. K. Kim, D. W. Kim, J. O. Kim, B. J. Lee, C. S. Yong, H. G. Choi, *Int. J. Pharm.,* 422 (2011) 202-210.

[08] R. Kaza, Y. P. Raju, R. Nagaraju, *Der Pharmacia Lettre,* 5 (2013) 126-134.

[09] D. Medarevic, S. Cvijic, V. Dobricic, M. Miodrag, J. Djuris, S. Ibric, *Eur. J. Pharm. Sci.,* 124 (2018) 188-198

[10] A. Karagianni, K. Kachrimanis, I. Nikolakakis, *Pharmaceutics,* 10 (2018) 98.

[11] Y. Huang, Q. Zhang, J. R. Wang, K. L. Lin, X. Mei, *Pharm. Dev. Technol.,* 22 (2017) 69-76.

[12] Y. Gao, L. Lei, B. Yang, J. Zhang, Y. Wei, S. Qian, zgtoszenie patentowe CN108794418A (2018).

[13] A. Lodagekar, R. B. Chavan, N. Chella, N. R. Shastri, *Cryst. Growth Des.* 18 (2018) 1944-1950.

[14] A. Lodagekar, R. B. Chavan, M. K. C. Mannava, B. Yadav, N. Chella, A. K. Nangia, N. R. Shastri, *Eur. J. Pharm. Sci.* 139 (2019) 105048.

[15] J. Haneef, R. Chadha, *AAPS PharmSciTech,* 18 (2017) 2279-2290.

[16] M. Vaduganathan, O. Vardeny, T. Michel, J. J. V. McMurray, M. A. Pfeffer, S. D. Solomon, *N. Engl. J. Med.,* 382 (2020) 1653-1659.

[17] J. K. Aronson, R. E. Ferner, *BMJ,* 369 (2020), 1313.

[18] Y., Liu, F. Huang, J. Xu, P. Yang, Y. Qin, M. Cao, Z. Wang, X. Li, S. Zhang, L. Ye, J. Lv, J. Wei, T. Xie, H. Gao, K.-F. Xu, F. Wang, L. Liu, C. Jiang, *medRxiv,* 2020.03.20.20039586 (preprint).

[19] A. Magaziner, B. S. Yasgur, All-Natural Cardio Cure: A drug-free cholesterol and cardiac inflammation reduction program, Penguin, 2004, ISBN: 1-58333-179-4.

[20] A. Nagai, H. Matsumiya, M. Hayashi, S. Yasui, H. Okamoto, K. Konno, *Exp. Lung Res.* (1994), 20(4), 263-281.

[21] Y. Shi, Y. Wang, C. Shao, J. Huang, J. Gan, X. Huang, E. Bicci, M. Piacentini, G. Ippolio, G. Melino, *Cell Death and Differ.* (2020), 27, 1451-1454.

[22] S. Kummar, A. Chen, R. E. Parchment, R. J. Kinders, J. Ji, J. E. Tomaszewski, J. H. Doroshow, *BMC Medicine* (2012), 10, 25.

[23] L. Zhang, Y. Liu, *J. Med. Virol* (2020), 92(5), 479-490.

[24] H. D. Jones, J. Yoo, T. R. Crother, P. Kyme, A. Ben-Shlomo, R. Khalafi, C. W. Tseng, W. C. Parks, M. Arditi, G. Y. Liu, K. Shimada, PLOS ONE (2015), 10(5), e0128735.

Research work on the co-amorphous solid dispersion of valsartan, the method of its synthesis and its medical application was financed by the NCN Preludium project no. UMO-2019/33/N/ST5/01602 entitled "Co-crystallization and co-amorphization of angiotensin II receptor blockers leading to more soluble compounds with a bifunctional character".

The invention claimed is:

1. Solvated co-amorphous solid dispersion of valsartan, comprising: valsartan present at a molar content of more than 40 mol %;

at least one non-toxic co-former having a molecular weight below 900 g/mol and being capable of forming hydrogen bonds with valsartan molecules, wherein the at least one non-toxic co-former comprises nicotinamide, and wherein the content of nicotinamide in the solid dispersion is equimolar to that of valsartan;

at least one non-toxic amphiphilic solvent selected from ethanol, n-propanol, i-propanol, anhydrous ethanol, anhydrous n-propanol, anhydrous i-propanol, and mixtures thereof, wherein the at least one non-toxic amphiphilic solvent solvates valsartan and nicotinamide and is present in the solid dispersion at a molar content of more than 2 mol %; and the solid dispersion exhibiting a water solubility greater than 3.5 times the water solubility of valsartan used for preparation of the same.

2. The solvated co-amorphous solid dispersion of claim 1, wherein the content of valsartan in the solvated co-amorphous solid dispersion exceeds 45 mol %.

3. The solvated co-amorphous solid dispersion of claim 2, wherein the content of valsartan in the solvated co-amorphous solid dispersion ranges from 46 to 49 mol %.

4. The solvated co-amorphous solid dispersion of claim 1, wherein the at least one co-former and the at least one amphiphilic solvent have a therapeutic effect supporting the effect of valsartan.

5. The solvated co-amorphous solid dispersion of claim 1, wherein the molar content of the at least one amphiphilic solvent in the solid dispersion is more than 5 mol %.

6. A pharmaceutical composition comprising the solvated co-amorphous solid dispersion of claim 1.

7. The pharmaceutical composition of claim 6, wherein the dispersion is useful for preparation of a medicament useful in treatment of hypertension.

8. The pharmaceutical composition of claim 7, wherein the composition is used for the manufacture of a medicament useful in treatment of SARS-COV-2 coronavirus infection causing COVID-19 disease, in one or more of prevention of development of the disease, enhancement of the immune response to the SARS-COV-2 virus, or an anti-inflammatory action in case of lung injury induced by ventilator used to treat the symptoms of acute respiratory distress syndrome associated with COVID-19.

9. A method for synthesizing a solvated co-amorphous solid dispersion of valsartan, comprising:

mixing valsartan with at least one non-toxic co-former having a molecular weight below 900 g/mol and being capable of forming hydrogen bonds with valsartan molecules to form a mixture, wherein the at least one non-toxic co-former comprises nicotinamide and the nicotinamide is combined in an amount equimolar to the valsartan;

adding a solvent over the mixture, wherein the solvent comprises at least one non-toxic amphiphilic solvent selected from ethanol, n-propanol, i-propanol, anhydrous ethanol, anhydrous n-propanol, anhydrous i-propanol, and mixtures thereof, the at least one non-toxic amphiphilic solvent solvating the valsartan and the nicotinamide;

mixing and homogenizing the solvent in a condensed-phase at a temperature range from 20° to 100° C.;

evaporating the solvent, wherein the solvent is stripped off at the temperature range of 20° to 100° C.; and recovering the solvated co-amorphous solid dispersion of valsartan, wherein the valsartan is present at a molar content of more than 40 mol %, the at least one non-toxic amphiphilic solvent is present at a molar content of more than 2 mol %, and the solid dispersion exhibits a water solubility greater than 3.5 times the water solubility of valsartan used for preparation of the same.

10. The method according to claim 9, wherein an additional drying step of the product is carried out under vacuum at a temperature range of 45 to 100° C.

11. The method according to claim 9, wherein the mixture comprising valsartan, nicotinamide, and an amphiphilic solvent has a 1:1 valsartan to nicotinamide molar ratio and a 1:6.9 to 1:9.7 valsartan to the solvent volume ratio; wherein the mixture is mixed in a closed system at the temperature range of 20 to 100° C. for 1 to 10 hours; wherein the evaporation of the solvent step is carried under vacuum in a rotary evaporator to give the solvated co-amorphous solid dispersion of valsartan of claim 9; and drying said dispersion.

12. The method according to claim 9, wherein the molar ratio of valsartan to nicotinamide is 1:1 and the volume ratio of valsartan to the solvent is from 1:0.83 to 1:2.48; subjecting the mixture to mechanochemical grinding at the temperature range of 20 to 70° C., for 0.5 to 10 hours to yield a crude product; dissolving the crude product in the solvent; stripping off the excess solvent at a temperature range of 20 to 100° C. under vacuum in a rotary evaporator to yield the solvated co-amorphous solid dispersion of valsartan of claim 9; and drying said dispersion.

13. The method according to claim 9, wherein the mixture has a 1:1 molar ratio of valsartan to nicotinamide and a 1:0.83 to 1:2.48 volume ratio of valsartan to the solvent; subjecting the mixture to mechanochemical grinding in a ball or disc mill at the temperature range of 20 to 70° C. for 0.5 to 10 hours to obtain a crude product; dissolving the crude product in the solvent; stripping off the excess solvent from the dissolved crude product at a temperature range of 20 to 100° C. under vacuum in a rotary evaporator to give the solvated co-amorphous solid dispersion of valsartan of claim 9; and drying said dispersion.

* * * * *